United States Patent [19]

Daffern et al.

[11] Patent Number: 4,994,238

[45] Date of Patent: Feb. 19, 1991

[54] CONSTANT VOLUME CHEMICAL ANALYSIS TEST DEVICE

[76] Inventors: George M. Daffern, 1672 Wright Ave., Sunnyvale, Calif. 94087; Tracy N. Thompson, 814 Moreno Ave., Palo Alto, Calif. 94303

[21] Appl. No.: 205,230

[22] Filed: Jun. 9, 1988

[51] Int. Cl.⁵ ............................................. G01N 31/22
[52] U.S. Cl. ..................................... 422/56; 422/57; 422/58; 436/170
[58] Field of Search ........................... 422/56, 57, 58; 436/170

[56] References Cited

U.S. PATENT DOCUMENTS

| | | |
|---|---|---|
| Re. 29,725 | 8/1978 | Johnson et al. . |
| Re. 30,267 | 5/1980 | Bruschi . |
| 2,912,309 | 11/1959 | Free . |
| 2,981,606 | 4/1961 | Keston . |
| 3,061,523 | 10/1962 | Free . |
| 3,092,465 | 6/1963 | Adams et al. . |
| 3,158,532 | 11/1964 | Pall . |
| 3,290,228 | 12/1966 | Gretton et al. . |
| 3,298,789 | 1/1967 | Mast . |
| 3,476,515 | 11/1969 | Johnson et al. . |
| 3,552,928 | 1/1971 | Fetter . |
| 3,558,435 | 1/1971 | Rey et al. . |
| 3,630,957 | 12/1971 | Rey . |
| 3,672,845 | 6/1972 | Verbeck . |
| 3,723,064 | 3/1973 | Liotta . |
| 3,783,105 | 1/1974 | Moyer et al. . |
| 3,847,553 | 11/1974 | Verbeck . |
| 3,914,174 | 10/1975 | Fuchs . |
| 3,917,453 | 11/1975 | Milligan et al. . |
| 3,964,870 | 6/1976 | Tiedemann et al. . |
| 3,975,162 | 8/1976 | Renn . |
| 3,980,437 | 9/1976 | Kishimoto et al. . |
| 3,992,158 | 11/1976 | Przybylowicz et al. . |
| 3,993,451 | 11/1976 | Verbeck . |
| 4,042,335 | 8/1977 | Clement . |
| 4,066,403 | 1/1978 | Bruschi . |
| 4,098,574 | 7/1978 | Dappen . |
| 4,144,306 | 3/1979 | Figueras . |
| 4,160,008 | 7/1979 | Fenocketti et al. . |
| 4,166,093 | 8/1979 | Smith-Lewis et al. . |
| 4,176,008 | 11/1979 | Figueras . |
| 4,178,153 | 12/1979 | Sodickson . |
| 4,211,845 | 7/1980 | Genshaw et al. . |
| 4,219,334 | 8/1980 | Schluter . |
| 4,231,754 | 11/1980 | Vogelhut . |
| 4,250,257 | 2/1981 | Lee et al. . |
| 4,255,384 | 3/1981 | Kitajima et al. . |
| 4,256,693 | 3/1981 | Kondo et al. . |
| 4,260,392 | 4/1981 | Lee . |
| 4,281,062 | 7/1981 | Kallis . |
| 4,292,272 | 9/1981 | Kitajima et al. . |
| 4,298,688 | 11/1981 | Kallies . |
| 4,318,985 | 9/1982 | Bauer et al. . |
| 4,361,648 | 11/1982 | Shuenn-Tzong . |
| 4,363,874 | 12/1982 | Greenquist . |
| 4,387,990 | 6/1983 | Yazawa et al. . |
| 4,390,343 | 6/1983 | Walter . |
| 4,391,905 | 7/1983 | Bauer . |

(List continued on next page.)

FOREIGN PATENT DOCUMENTS

| | | | |
|---|---|---|---|
| 0123443 | 3/1984 | European Pat. Off. ............. | 422/57 |
| 256806 | 2/1987 | European Pat. Off. . | |

*Primary Examiner*—Robert J. Warden
*Assistant Examiner*—Jill Johnston
*Attorney, Agent, or Firm*—William B. Walker

[57] ABSTRACT

The multilayer test devices of this invention comprise, in order, (a) an absorbent layer; (b) a waterproof barrier layer; and (c) a quickly absorbent reagent layer having a determinate volume. The absorbent and barrier layers each include an aperture functionally aligned for application of a test sample through the absorbent and barrier layers and onto the surface of the reagent layer. The reagent layer contains one or more reagents which produce a detectable species in the presence of an analyte. The reagent layer preferably comprises an asymmetrical filter, which localizes cellular components of the test sample at or near the surface of the filter, while facilitating saturation of the filter by non-cellular sample components. Preferred embodiments of the test devices include devices for testing glucose, alcohol, cholesterol, or other analytes in whole blood.

5 Claims, 4 Drawing Sheets

U.S. PATENT DOCUMENTS

| | | | |
|---|---|---|---|
| 4,391,906 | 7/1983 | Bauer. | |
| 4,427,632 | 1/1984 | Okaniwa et al.. | |
| 4,438,067 | 3/1984 | Siddiqi. | |
| 4,452,887 | 6/1984 | Kitajima et al.. | |
| 4,476,222 | 10/1984 | Ohtani et al.. | |
| 4,477,575 | 10/1984 | Vogel et al.. | |
| 4,478,942 | 10/1984 | Katsuyama et al.. | |
| 4,478,944 | 10/1984 | Gross et al.. | |
| 4,532,107 | 7/1985 | Siddiqi. | |
| 4,540,670 | 9/1985 | Arai et al.. | |
| 4,543,338 | 9/1985 | Chen. | |
| 4,587,099 | 5/1986 | Rothe et al.. | |
| 4,594,224 | 6/1986 | Okaniwa. | |
| 4,594,327 | 6/1986 | Zuk. | |
| 4,604,264 | 8/1986 | Rothe et al.. | |
| 4,621,049 | 11/1986 | Wang. | |
| 4,631,174 | 12/1986 | Kondo. | |
| 4,632,901 | 12/1986 | Valkirs. | |
| 4,637,978 | 1/1987 | Dappen. | |
| 4,647,430 | 2/1987 | Zweig. | |
| 4,668,472 | 5/1987 | Sakamoto et al.. | |
| 4,678,757 | 7/1987 | Rapkin et al.. | |
| 4,738,823 | 4/1988 | Englemann. | |
| 4,774,192 | 9/1988 | Terminiello. | |
| 4,780,280 | 10/1988 | Berger et al. | 422/56 |
| 4,786,596 | 11/1988 | Adams | 422/56 |
| 4,814,142 | 3/1989 | Gleisner | 422/56 |
| 4,818,677 | 4/1989 | Hay-Kaufman et al. | 422/56 |
| 4,824,639 | 4/1989 | Hildenbrand et al. | 422/58 |

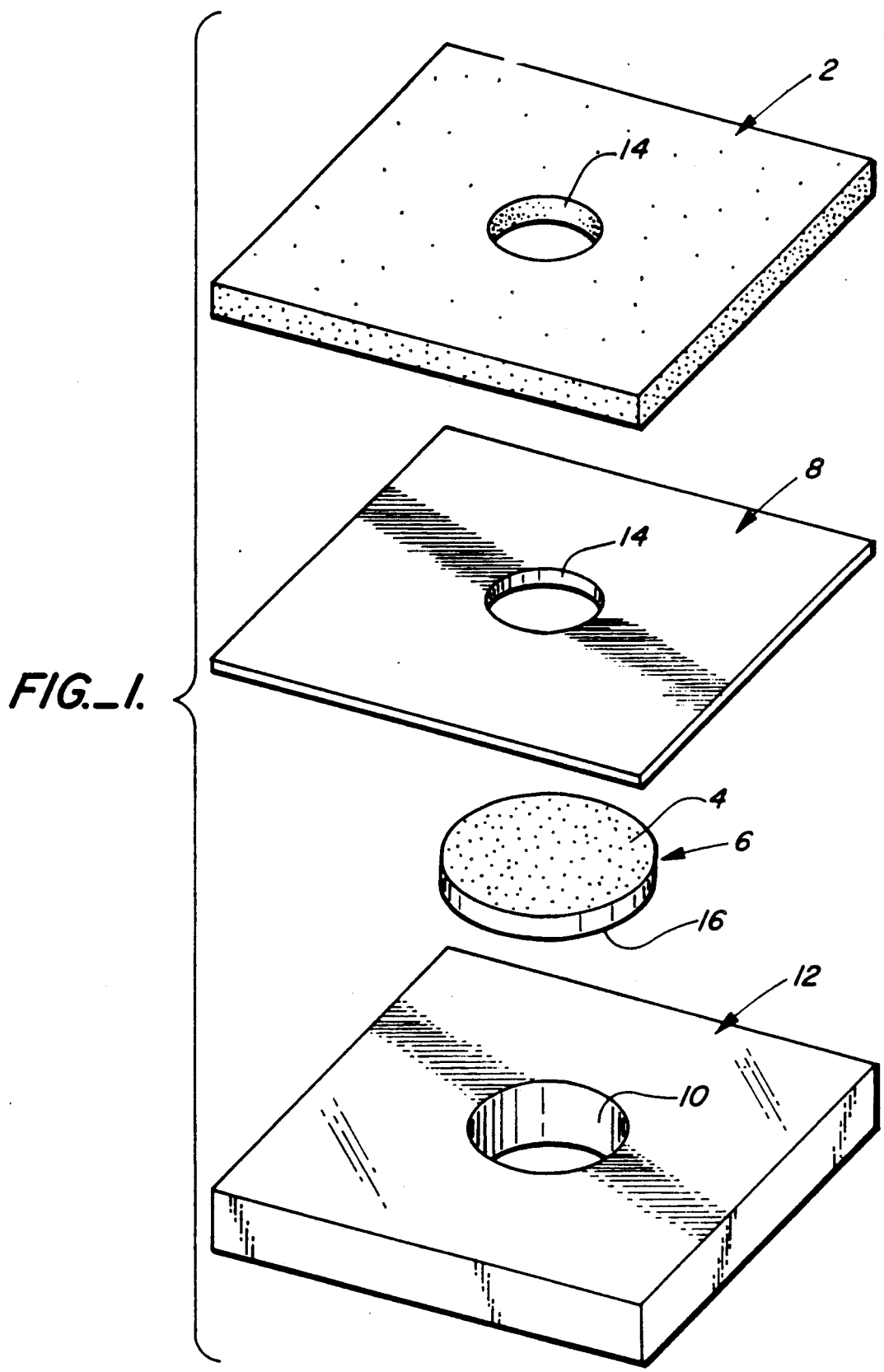
FIG._1.

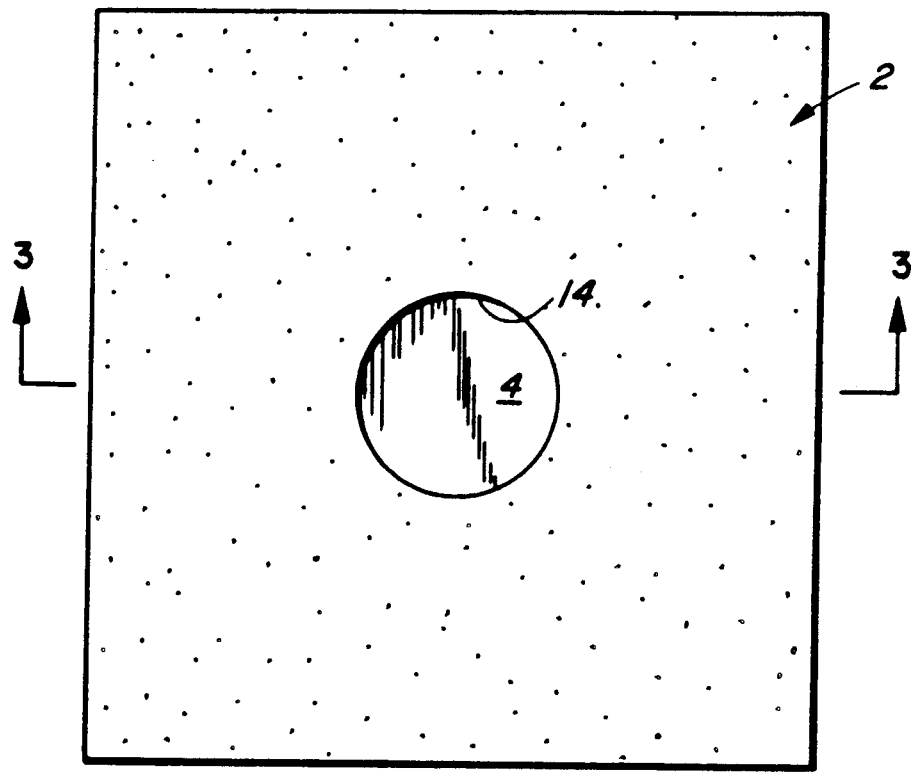
FIG._2.
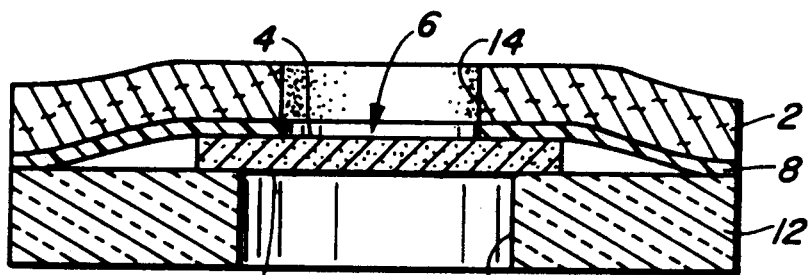
FIG._3.
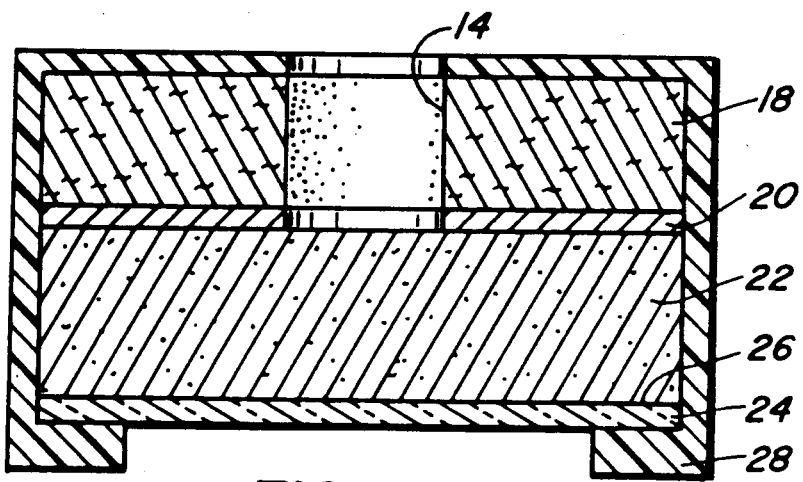
FIG._4.

CONSTANT VOLUME CHEMICAL ANALYSIS TEST DEVICE

FIELD OF THE INVENTION

The invention relates to an improved, disposable device for chemical analysis of liquids. More particularly it concerns multilayer elements that provide a means for determining the presence and/or concentration of an analyte in a liquid by effecting the release or formation of a detectable species, such as a dye, within the element, in quantities proportionate to the concentration of the analyte.

BACKGROUND OF THE INVENTION

Multilayer test elements have been extensively used in laboratory environments to determine an analyte of interest. Multilayer reagent strips are shown in U.S. Pat. No. 3,672,845. U.S. Pat. Nos. 3,993,451 and 4,438,067 disclose the use of particulated reagents, and U.S. Pat. No. 3,723,064 discloses the use of a membrane having regions of differing permeability. U.S. Pat. No. 3,783,105 demonstrates the use of freeze-dried reagents. Other multilayer test designs are shown by U.S. Pat. Nos. 3,980,437, 4,042,335, 4,144,306, 4,160,008, 4,178,153, 4,292,272, 4,318,985, 4,387,990, 4,427,632, 4,452,887, 4,532,107, 4,604,264, and 4,668,472. Another alternative to the multilayer test device approach is shown in U.S. Pat. No. 3,476,515, which discloses rupturable sample and reagent pouches. U.S. Pat. No. 3,158,532 teaches the manufacture of a filter which has pores of graduated size and filtration capacity.

Specific reagents have been found useful in assays for the presence of glucose, cholesterol, alcohol, and other analytes (see, for example, U.S. Pat. Nos. 2,912,309 and 2,981,606). Buffers, stabilizers, dyes, and other detectable moieties have been incorporated into multilayer devices and test strips.

One difficulty in the prior art has been accurate dosing of the test sample into or onto the assay device. Quantitative evaluation for an analyte has generally involved careful control of sample volume. Reagents in the test device are allowed to react completely with the sample, and the extent of reaction determined. Analyses which do not involve sample control have generally been semi-quantitative or qualitative, rather than quantitative tests.

The presence of red blood cells in whole blood samples may cause interference in the detection of color changes. Cellular components in blood have been blocked or filtered from the determining layer by use of cellulose (U.S. Pat. No. 3,092,465), amino acids (U.S. Pat. No. 3,552,928), glass fibers (U.S. Pat. No. 4,477,575), or carbohydrate (U.S. Pat. No. 4,678,757). Fluid metering with the concurrent removal of cellular components of blood is addressed in U.S. Pat. Nos. 4,250,257 and 4,260,392.

Barrier or blocking layers have been used to segregate cellular components from the serum portion of a whole blood sample. Such barriers used in prior art elements generally are required to be permeable to the ligand, the reagents of the reagent layer, or products of their interaction. In such devices, determination of the detectable species is made from the detecting layer surface away from the reagent layer. Alternatively, a barrier may be included on the element to confine an applied sample to a predetermined region of the element surface. Barrier layers in multilayer elements are shown in U.S. Pat. Nos. 3,992,158, 4,166,093, 4,255,384, 4,256,693, 4,363,874, 4,390,343, 4,478,944, 4,631,174, and 4,066,403 (U.S. Pat. No. Re. 30,267).

SUMMARY OF THE INVENTION

The present invention provides a test device for a bodily fluid comprising, in sequential contact, an absorbent layer, a barrier layer, and a reagent matrix layer having a defined saturation volume, wherein the absorbent and barrier layers each includes an opening for applying a test sample directly onto the reagent layer. In one embodiment, a support is provided on a side of the reagent layer opposite the dosing surface. In an especially preferred embodiment, the support layer includes an aperture which permits contact between the lower layer of the reagent matrix layer and the atmosphere. In another embodiment, the reagent layer may be substantially enclosed, with the proviso that the barrier and absorbent layers include openings exposing a substantial portion of the reagent layer to the atmosphere.

In a preferred embodiment, the dosing surface of the reagent matrix layer constitutes a means for retaining cellular components.

One preferred embodiment comprises a test device and method for determining glucose in a whole blood sample. Other preferred embodiments are test devices and methods for cholesterol and alcohol determination in whole blood samples.

BRIEF DESCRIPTION OF THE DRAWINGS

FIG. 1 is an exploded view of a preferred embodiment of the test device of this invention.

FIG. 2 is a top view of a device of this invention showing the axis of cross-section for FIGS. 3 and 4.

FIG. 3 is a cross-sectional view of a preferred embodiment of the test device of this invention.

FIG. 4 is a cross-sectional view of another embodiment of the test device of this invention.

DETAILED DESCRIPTION OF THE INVENTION

FIG. 1 shows an exploded view of a test device of this invention. The absorbent layer 2 is separated from the dosing surface 4 of the reagent matrix 6 by the barrier layer 8. The optional support 12, in supporting relationship to the reagent layer 6 and the barrier layer 8, includes an aperture 10 through which the detectable species can be determined at the determination surface 16. An opening 14 through each of the absorbent layer 2 and barrier layer 8 allows deposition of a test sample onto the dosing surface 4 of the reagent matrix layer.

FIG. 2 is a top view of a device of this invention which demonstrates the axis of cross-section, along line c—c, for FIGS. 3 and 4.

FIG. 3 is a cross-sectional view of a preferred embodiment of a device of the invention. The absorbent layer 2 and barrier layer 8 define a hole 14 for application of the test sample onto the dosing surface 4 of the reagent matrix layer 6, which has a defined saturation volume. An opening 10 in the support layer 12 allows visual determination of a detectable species at the determination surface 16 of the reagent matrix 6.

FIG. 4 demonstrates an alternate embodiment of the test device wherein the support forms an enclosure which acts to hold the absorbent layer 18, barrier layer 20, and reagent layer 22 in close proximity while limiting exposure of the reagent matrix to the atmosphere. A substantially transparent support element 24 is held adjacent to the reagent matrix 22 at its determination surface 26 by an enclosing support 28. Support elements 24 and 28 may conveniently be manufactured as one unit.

The test device of this invention provides a fixed volume of sample into the reagent layer without volumetric measurement and provides a quantitative evaluation for the analyte in question. The reagent matrix is manufactured to provide a defined saturation volume. Adjacent to the dosing surface of the reagent matrix is a barrier layer. Adjacent to the barrier layer is an absorbent layer. Each of the barrier and absorbent layers includes an aperture or hole, for deposition of the test sample directly onto the dosing surface of the reagent matrix. The reagent matrix is quickly absorbent, and sample which is presented on its surface quickly saturates the reagent layer. Excess sample remains at the surface of the reagent matrix, where it is absorbed more slowly by the absorbent layer. The barrier layer separates the reagent matrix from the absorbent layer, so that the two absorbent layers are in fluid contact only while there is unabsorbed sample at the surface of the reagent matrix.

The amount of sample placed onto the reagent test device should be in excess of that required to fully saturate the reagent pad. When the reagent pad becomes saturated, further flow of sample into the reagent matrix stops. The remainder of the sample is absorbed by the absorbent layer. Excess sample in the absorbent layer remains separated from the reagent pad by the barrier layer and thereby does not affect the reaction.

The constant volume test devices of the present invention and the process for forming such test devices are suited to a broad range of volume sensitive solid phase test devices. These include assays for glucose, alcohol, AST (cholesterol), ALT (phenobarbital), theophylline and other chemical assays.

Located at one surface of the reagent matrix, and positioned between the reagent matrix and the absorbent layer, is the barrier layer. The barrier layer is a waterproof or substantially waterproof material which has at least one opening or aperture. The aperture may be of any shape, for example, square, rectangular, octagonal, ellipsoidal, etc., and is conveniently round. The aperture of the barrier layer may or may not be of similar size, shape, or configuration to that of the absorbent layer. However, the apertures of the two layers must align functionally so that a liquid sample to be tested is inserted conveniently through the openings in the absorbent and barrier layers, and onto the exposed surface of the reagent layer. Conveniently, the aperture is at least 0.050 inches in diameter, more generally at least 0.150 in., and preferably from 0.180 to 0.500 in. The barrier layer may be made from any convenient waterproof material, especially in the form of a sheet or foil. Metal sheets or foils include e.g., aluminum foil. Polymeric materials suitable for use include polyethylene, polypropylene, poly(vinyl chloride), cellulose acetates, polyethyleneterephthalates, polycarbonates, or polystyrenes. Various types of paper including paraffin-impregnated paper, polymer laminated paper, water-resistant paper, and wax paper are appropriate, as is glass. The barrier may or may not be composed of the same material as the support, if any. Alternatively, a solution of a waterproofing material which will form the barrier layer may be coated onto the absorbent layer. A suitable thickness of the waterproof barrier layer is about 3 microns to about 1 mm or less, and more preferably about 10 microns to about 0.4 mm.

Pressure-sensitive, thermosensitive, solvent-based, and reactive adhesives may be used as an adhesive to fix the barrier layer to the absorbent layer, the reagent matrix layer, and/or the support layer. Preferably, a double-sided adhesive tape is utilized to provide the waterproof barrier layer and to provide ease of assembly of the test device.

The absorbent layer is preferably a hydrophilic paper, but other absorbent materials can also be used. Open-pored synthetic resin foams, blush polymers, liquid resistant gels, fabrics, felts, and the like may be used. Inorganic materials, for example, gypsum, are less preferred since they normally do not possess sufficient stability. The absorbency of these materials should be such that, upon contact of a test sample with the surface of the reagent matrix, the edge of the absorbent layer is moistened, but the test sample is substantially absorbed by the reagent layer until the reagent layer is saturated. Generally, the absorbent layer will be more slowly absorptive than the reagent layer. Reagent layer saturation should be achieved in about one-half second to two seconds or less. Excess sample which remains on the surface of the reagent layer should be absorbed by the absorbent layer within 0.5 to 60 seconds, preferably within 1 to 30 seconds, more preferably 1 to 5 seconds. The detectable species is fully formed, and the assay is ready for determination of the detectable species after 1 minute or less, preferably 30 to 45 seconds, more preferably less than 30 seconds.

The absorbent layer includes at least one opening or aperture through which a test sample may be deposited on the reagent matrix surface. This aperture should generally coincide with the aperture in the barrier layer so that a functional unit is formed. However, the apertures in each of the absorbent and barrier layers need not be of identical size or location relative to each other, as long as functionality is not diminished.

In a preferred embodiment, an aperture is provided through the support member to allow exposure of the determining surface 16 of the reagent matrix layer 6 to the atmosphere, and to permit visual or spectrophotometric determination of the detectable species. It is an advantage of this embodiment that atmospheric oxygen is accessible to both surfaces of the reagent matrix by means of the apertures through the barrier, absorbent, and support layers. Analyses which are preferably performed while exposed to atmospheric oxygen are easily accommodated by minimizing support surfaces and maximizing the surface area of the reagent matrix which is exposed to the atmosphere.

In another embodiment for assays wherein it is advantageous to permit contact between reagents or reagent products and the atmosphere, the reagent matrix may be provided with a base support or carrier, leaving lateral surfaces unsupported and open to the atmosphere.

The nature of the support is not particularly limited, as long as it is impermeable to liquid, and can transmit light or other means necessary for determining the detectable species if required. For example, various polymeric materials, such as polyethylene terephthalates, polycarbonates or polystyrenes, or materials such as glass, or wax paper are suitable for this purpose. The support employed may have any desired thickness, but generally a thickness of about 50 microns to about 2 millimeters is adequate. When the reagent layer is provided directly on the support, it may be directly coated thereon. When the reagent layer is a sponge-like material, it may be desirable to glue or otherwise laminate or affix the reagent layer to the support. Alternatively, the support may form an enclosure, acting to hold the reagent layer, barrier layer, and absorbent layer in close proximity.

Suitable supports may be opaque or transparent. If no aperture through the support is provided, it is preferable that the support be substantially transparent, so that determination of the detectable species may be made through the support, either visually or by mechanical reading.

In an alternate embodiment of the test device, no support or holder is provided, and the test device consists of a reagent layer, barrier layer, and absorbent layer laminated together in that order. Such devices may be placed on any convenient surface when the assay is conducted. In another embodiment, the reagent matrix is enclosed within a holder, such that only the surface area which is coincident with the aperture in the absorbent and barrier layers is exposed. Such a configuration is shown in FIG. 4.

The reagent matrix layer is a quickly absorptive, hydrophilic region which performs three functions: (1) it provides a determinate volume for reagents and the test sample; (2) it filters cellular components of the test sample such that cellular components are retained at, or close to, the surface of the matrix, while non-cellular liquid sample is transported throughout the matrix; and (3) it provides an appropriate sensing region for determination of the presence of detectable species, free from background interference from red blood cells or other cellular components of the test sample.

Materials which are appropriate for use as the reagent matrix base layer include glass fibers and foam filters of the prior art. Preferably, the reagent matrix base layer comprises a porous member which is asymmetrically porous, having pores of progressively decreasing diameter in a progression from the upper (dosing) surface to the lower (determining) surface. A blown-pore or open-pore structure such as that found in the RTS Asymmetric membrane from Brunswick or that shown by U.S. Pat. No. 3,158,532, issued to Pall et al., is especially preferred. Such membranes have the advantage of acting to separate cellular blood components: when a test sample comprising whole blood is applied to the test device, red blood cells are localized at the dosing surface. Serum blood components progress throughout the porous medium, and the reagent-analyte reaction occurs throughout the matrix. The lower reagent matrix surface provides a region where the detectable species is determined without interference by red blood cell pigmentation.

It is an advantage of this invention that the volume of the reagent layer upon sample saturation may be precisely calculated, as any excess sample is absorbed by the absorbent layer. The exact amount of reagent necessary for quantitative analysis of the analyte in the test sample may be calculated and provided within the reagent matrix.

In use, the amount of excess sample applied to the exposed surface of the matrix becomes unimportant, within wide tolerances. Non-cellular components of the sample placed on the dosing surface of the reagent matrix pass into the matrix until the reagent matrix pad is saturated. Upon pad saturation, the excess sample remains on top of the matrix layer, where it is absorbed by the absorbent layer and is prevented from reacting with reagents in the matrix pad by the barrier layer. Accordingly, the resulting test device achieves constant loading of sample per unit regardless of the amount of sample applied to the test device and a constant volume test device is obtained. A device designed to accept a droplet of sample to be tested is easily designed so that only a fraction of a standard drop is necessary to fully saturate the reagent matrix. The absorbent layer is designed so that an excess volume, for example twice, preferably 10 times or greater, of the suggested load for saturation of the reagent matrix may be absorbed by the absorbent layer. Test devices may be designed to accept a wide variety of sample loads, and specific designs will be apparent to those skilled in the art in view of the teachings herein.

In a preferred embodiment, the reagent matrix includes a single membrane or filter medium which exhibits progressively finer filtration in a progression from the dosing surface to the lower surface, so that cellular components of the test sample are localized at the upper surface of the membrane. This medium may be opaque, and have light or dark color characteristics. When the detectable species is a dye, it is preferable to have an opaque, light-colored or white background, for color detection.

The reagent matrix layer includes one or more chemical reagents which are capable of directly or indirectly reacting with the analyte of interest to produce a detectable species. Reagents which give rise to a colored reaction product or cause a distinct change in color are preferred for ease of reading. Reagents which provide chemiluminescence, or other detectable products, are also appropriate for use. Specialized apparatus for determining the extent of reaction may be necessary for non-visually determinable products.

The substances in blood, serum, urine, cerebrospinal fluid, lymph, or other bodily fluid, which can be measured by the test device of this invention include glucose, galactose, pyruvic acid, amino acids, cholesterol, lactic acid, alcohol, urea, etc. The reagents used for measurement are determined individually depending upon the analyte to be measured. For example, a test device for measuring glucose in blood may contain glucose oxidase, a substance having peroxidase activity, and an oxidizable indicator as ingredients. Similarly, a test device for measuring galactose in blood may contain galactose oxidase, a substance having peroxidase activity, and an oxidizable indicator. Where the alcohol level in blood is to be measured, a test device may be impregnated with a reagent system comprising alcohol dehydrogenase, nicotine adenine dinucleotide, diaphorase and a tetrazolium salt.

The detectable species of the reagent layer may be varied to facilitate the detection process. The terms "detectable chemical species" and "detectable species" refer to a chemical species which provides a detectable signal or change that is directly or indirectly indicative of the presence and/or concentration of a desired analyte, or a reaction or decomposition product of the analyte, e.g., the optical density of a color formed, fluorometric density, electromagnetic (including radiation) intensity or a change in these densities or intensities. Preferably, the detectable change that is produced is optically detectable, e.g., visually detectable, or detectable using spectrophotometry. In a preferred embodiment, the detectable species is determined at the determination surface 26.

The preferred dyes or other detectable chemical species will differ for various assays, and are well known to those skilled in the art. Exemplary of dyes which are appropriate for use in an assay for glucose in a body fluid are 3,5-Dimethylaminobenzoic acid (DMAB); 3-Methyl-2-benzothiazolinone hydrazone hydrochloride (MBTH); and/or tetramethyl benzadine (TMB). A preferred dye is DMAB, which shows an absorption peak at 570–600 nm. A device such as a spectrophotometer may to be used to determine the dye produced. The dye is conveniently determined at 570–600 nm. This preferred dye and determination wavelength act to minimize the background interference when red blood cells are present at the dosing surface of the reagent matrix layer.

In most cases, the means for measuring a specific analyte is not limited to only one set of reagents, and a plurality of suitable reagents are known. Any chemical method may be applied as long as the reagent can be contained in the reagent matrix in a stable state. Further, one may add a substance to buffer the regent composition to a constant pH, a substance to stabilize it, a hydrophilic substance to aid absorption of the test sample into the matrix, a substance to adjust the reaction rate, etc., and it is well appreciated by those skilled in the art that the present invention may be easily modified based on such conventional knowledge.

The general structure and function of elements of the test device of this invention have been described. For purposes of clarity and not by way of limitation, the device, and methods of making and use will be described for a quantitative glucose assay which permits optical determination, and which may preferably be determined using a spectrophotometer.

Appropriate reagents, buffers, and chromogen materials are dissolved into an aqueous solvent to produce a second solution. In an assay for glucose, an enzyme system having glucose oxidase activity is provided, together with a substance having peroxidative activity and a substance capable of undergoing a color change upon reaction with one or more of the compounds formed during the action of the enzyme upon glucose containing fluids. Substances having peroxidative activity which are useful in the present invention can be chosen from various organic and inorganic sources, and are well known to those skilled in the art.

The filter medium is dipped into the solution and dried. The filter may be wrung or squeezed prior to drying, to hasten the drying time.

The coated reagent matrix may be cut into smaller units, or otherwise processed into the test devices of this invention. The openings in the covering absorbent and barrier layers may be formed either before or after (but normally before) the absorbent and barrier layers have been applied to the reagent matrix. The layers may be laminated together, applied by chemical deposition, or contained in an enclosing holder. In an especially preferred embodiment, the barrier layer comprises double-sided tape and acts to laminate the reagent layer, the absorbent layer, and the support layer together.

To measure glucose in blood, a blood drop taken from the earlobe, finger tip, or other blood source, is applied to the dosing surface of the reagent matrix. Glucose which is present in the fluid sample is converted to gluconic acid by glucose oxidase. Hydrogen, released by this reaction, combines enzymatically with atmospheric oxygen to form hydrogen peroxide. In the presence of a peroxidase, hydrogen peroxide oxidizes the indicator, producing a determinable color. Generally, the detectable species is formed in two minutes or less, preferably three seconds or less, from the time of dosing of the test sample. The concentration of glucose is calculated by comparing the color produced with a standard color chart which is prepared separately.

If a mechanical device is to be used to determine the glucose optically, the reflectance of the color produced is measured at a predetermined wavelength by means of an appropriate measuring instrument, e.g. a spectrophotometer. The concentration of glucose is determined with reference to a concentration-reflectance curve which is prepared separately.

A device according to this invention to assay for alcohol in a test sample comprises, sequentially, an absorbent layer, a barrier layer, and a reagent matrix layer including a chemical system which produces a detectable species in the presence of alcohol, such as alcohol oxidase, peroxidase, and a suitable dye. Apertures through the absorbent and barrier layers are provided. A test sample, such as a drop of whole blood, serum, urine, or other bodily fluid, is placed through the apertures and onto the dosing surface of the reagent matrix. The presence and extent of the detectable species is determined, as appropriate to the detectable species used. When the detectable species is a dye such as tetramethyl benzadine (TMB), the determination may be made visually, or with a spectrophotometer. The alcohol assay device produces a quick, quantitative assay without the need to accurately measure the sample provided to the dosing surface. A small sample, e.g., a drop of whole blood, is sufficient to provide results. The device may be made as a disposable unit. When a colorfast dye is used, the device may be retained to provide evidence of the assay. The device is not particularly temperature sensitive, and may be used in a variety of field conditions, e.g., roadside checkpoints for alcohol use while operating a motor vehicle.

A device according to this invention to assay for cholesterol in a test sample comprises, sequentially, an absorbent layer, a barrier layer, and a reagent matrix layer including a chemical system which produces a detectable species in the presence of cholesterol, such as cholesterol esterase, cholesterol oxidase, and peroxidase with a suitable dye. Apertures through the absorbent and barrier layers are provided. A test sample, such as a drop of whole blood, serum, or plasma, is placed through the apertures and onto the dosing surface of the reagent matrix. The presence and extent of the detectable species is determined, as appropriate to the detectable species used. When the detectable species is a dye such as TMB, the determination may be made visually, or with a spectrophotometer. The device may be used for continued monitoring of a patient's cholesterol levels in a disposable home test. The cholesterol assay device produces a quick, quantitative assay without the need to accurately measure the sample provided to the dosing surface. A small sample, i.e., a drop of blood, is sufficient. Instructions are simple, and only minimal training is required for accurate use of the device.

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Glucose Reagent Matrix

SOLUTION A: 0.50 to 1.00 g cellulose acetate is slowly added to 50 ml glacial acetic acid and stirred rapidly until completely dissolved. 50 ml isopropanol is then slowly added with stirring. As the final volume is approached, the alcohol is added dripwise to prevent precipitation of the cellulose from the solution. To this solution, 3.00 g. 3,5-Dimethylaminobenzoic acid (DMAB) is added and stirred until dissolved. It may be necessary to add a few drops of 5.0M NaOH to complete solvation of the acid.

Brunswick BTS asymmetric polysulfone membrane is dipped in this solution and air dried until the alcohol and acetic acid have evaporated, approximately ten minutes at 50° C.

SOLUTION B: A second dip is prepared by dissolving 10.00 g polyvinylpyrollidone (PVP) in approximately 60 ml of water. Some heating may be required to enhance solvation. To this solution, 12.0 ml of a filtered 25% acacia solution is added, followed by 0.1 ml FC-129, 0.400 g 3-Methyl-2-benzothiazolinone hydrazone hydrochloride (MBTH), and competitor. 10.00 ml TRIS 1 M (pH 7.5) and 5.00 ml citrate 1M (pH 7.5) are added slowly, to prevent crystallization of the chromogen, and the pH is adjusted to 7.5±0.1. After adjustment of the solution, 50,000 U glucose oxidase and 50,000 U peroxidase are added to the solution. Final volume is adjusted to 100.0 ml.

The membrane which had been dipped in Solution A and dried is dipped in this solution and air dried until the solvent has evaporated, approximately ten minutes at 50° C.

EXAMPLE 2

Alcohol Reagent Matrix

A first solution is formed by the process used for Solution A in Example 1, using the following: 0.50 to 1.00 g cellulose acetate; 50 ml glacial acetic acid; 50 ml isopropanol; 3.00 g 3,5-Dimethylaminobenzoic acid (DMAB).

Dipping and drying of the membrane follow the procedure of Example 1.

A second solution is prepared according to the process of Solution B of Example 1, using 10.00 g polyvinylpyrollidone (PVP) in approximately 60 ml of water; 12.0 ml of a filtered 25% acacia solution; 0.1 ml FC-129, 0.400 g 3-Methyl-2-benzothiazolinone hydrochloride (MBTH), and competitor; 10.00 ml TRIS 1M (pH 7.5) and 5.00 ml citrate 1 M (pH 7.5). 30,000–50,000U alcohol oxidase and 30,000–50,000U peroxidase are added to the pH adjusted solution. Final volume is adjusted to 100.0 ml.

Dipping and drying of the membrane follow the procedure of Example 1.

EXAMPLE 3

Cholesterol Reagent Matrix

A first solution is formed by the process shown in Example 1, using 0.50 to 1.00 g cellulose acetate; 50 ml glacial acetic acid; 50 ml isopropanol; 3.00 g 3,5-Dimethylaminobenzoic acid (DMAB). pH is adjusted as necessary.

Dipping and drying of the membrane follow the procedure of Example 1.

A second solution is prepared according to the process of Solution B of Example 1, using 10.00 g polyvinylpyrollidone (PVP); 60 ml of water; 12.0 ml of a filtered 25% acacia solution; 0.1 ml FC-129, 0.400 g 3-Methyl-2-benzothiazolinone hydrazone hydrochloride (MBTH), and competitor; 10.00 ml TRIS 1M (pH 7.5) and 5.00 ml citrate 1M (pH 7.5). 100–200 U cholesterol esterase, 100–200 U cholesterol oxidase, and 1000 U peroxidase are added to the pH adjusted solution. Final volume is adjusted to 100.0 ml.

Dipping and drying of the membrane follow the procedure of Example 1.

EXAMPLE 4

Construction of Test Device

A sheet of filter paper approximately 8 in. by 8 in. square is laminated to one surface of a tape having waterproof adhesive on both surfaces, such as 415 adhesive from 3M. Paper and tape are cut into ½ inch strips. A circular opening approximately 0.187 inches in diameter is made through both layers at 1 inch intervals along the tape. A reagent matrix according to Example 1 which has been trimmed to a 0.250 inch diameter is aligned with the circular opening, and applied to the exposed adhesive surface. A plastic strip ½ inch wide is aligned with and laminated to the filter paper/adhesive tape/membrane strip over the reagent matrix membrane. The strip is then cut into 1 inch segments, each segment containing a sample application aperture in the center. The saturation volume of the reagent matrix is approximately 3 Ml (microliters).

EXAMPLE 5

Glucose Testing of Blood Sample

A drop of blood from a finger puncture is placed onto the test device of Example 4 at the opening through the absorbent layer. The test device is allowed to stand for at least one second. The detectable species is determined using a spectrophotometer at 590 nm. The spectrophotometric result is compared to a standard curve to determine the quantity of glucose in the blood sample.

EXAMPLE 6

Alcohol Content of a Blood Sample

A test device is manufactured according to the process of Example 4, substituting the reagent matrix of Example 2 for that of Example 1. A drop of whole blood is placed onto the test device at the dosing surface. The dye production is evaluated at the determination surface using a spectrophotometer at 590 nm., and compared to a standard, to ascertain the amount of alcohol in the blood sample.

EXAMPLE 7

Cholesterol Content of a Blood Sample

A test device is manufactured according to the process of Example 4, substituting the reagent matrix of Example 3 for that of Example 1. A drop of whole blood is placed onto the test device at the exposed dosing surface. The dye production is visually evaluated at the determination surface and compared to a standard, to ascertain the amount of cholesterol in the blood sample.

EXAMPLE 8

Glucose Testing of a Urine Sample

A test device according to Example 4 is constructed. A drop of urine is placed at the opening through the absorbent layer. The test device is allowed to stand at least one second. The color is determined, and compared to a standard curve to determine the quantity of glucose in the urine sample.

What is claimed is:

1. A multilayer testing device comprising, in sequential contact,
   (a) an absorbent layer;
   (b) a waterproof barrier layer; and
   (c) a quickly absorbent reagent matrix layer having a determinate volume, and containing therein at least one reagent which produces a detectable species in the presence of an analyte;
   wherein the absorbent and barrier layers each include an aperture functionally aligned for application of a test sample through the absorbent and barrier layers and onto a surface of the reagent layer and the reagent layer comprises an asymmetrically porous membrane having progressively finer filtration with increased distance from the barrier layer.

2. A multilayer assay device for determining glucose in a whole blood sample, comprising, in sequential contact,
   (a) an absorbent layer;
   (b) a waterproof barrier layer;
   (c) a reagent matrix layer comprising an asymmetrically porous membrane which provides progressively finer filtration with increased distance from the barrier layer, and which contains at least one reagent which reacts with glucose in a liquid sample to produce a detectable species; and
   (d) a support layer including an aperture which allows the reagent matrix layer contact to the atmosphere;
   wherein the barrier layer and absorbent layer each contain an aperture which is functionally aligned to facilitate the deposition of a liquid test sample through the apertures and onto the surface of the reagent layer.

3. An assay device according to claim 2 wherein the reagent comprises 3,5-Dimethylaminobenzoic acid (DMAB), 3-Methyl-2-benzothiazolinone hydrazone hydrochloride (MBTH), glucose oxidase, and peroxidase.

4. An element in a multilayer test device comprising an absorbent, asymmetrically porous membrane providing progressively finer filtration with distance from a sample receiving surface, which membrane has a determinate saturation volume, and which acts to filter cellular components of a test sample at or near the sample receiving surface.

5. An element according to claim 4 further including one or more reagents which produce a detectable species in the presence of an analyte.

* * * * *